United States Patent [19]

Paciorek et al.

[11] 4,297,510
[45] Oct. 27, 1981

[54] UNSYMMETRICAL DIPHOSPHATETRAAZACYCLOOCTATETRAENES

[75] Inventors: Kazimiera J. L. Paciorek, Corona Del Mar; Reinhold H. Kratzer, Irvine; Thomas I. Ito, Fountain Valley; James H. Nakahara, Irvine, all of Calif.

[73] Assignee: The United States of America as represented by the Secretary of the Air Force, Washington, D.C.

[21] Appl. No.: 163,135

[22] Filed: Jun. 26, 1980

[51] Int. Cl.³ ............................ C07F 9/22; C10M 1/44
[52] U.S. Cl. ...................................... 564/13; 252/49.9; 252/73; 252/400 A; 252/389 A
[58] Field of Search ............ 564/13; 252/49.9, 400 A, 252/389 A

[56] References Cited

U.S. PATENT DOCUMENTS

| | | | |
|---|---|---|---|
| 3,304,270 | 2/1967 | Dickerson | 260/2 |
| 3,463,813 | 8/1969 | Dickerson | 564/13 |
| 3,711,542 | 1/1973 | Hook et al. | 564/13 |
| 3,846,374 | 11/1974 | Farley et al. | 564/13 |
| 4,166,071 | 8/1979 | Paciorek et al. | 564/13 |
| 4,215,072 | 7/1980 | Paciorek et al. | 252/49.9 X |

OTHER PUBLICATIONS

Zhur. Obshch. Khim., vol. 32, No. 9, (1962).

*Primary Examiner*—Charles F. Warren
*Attorney, Agent, or Firm*—Donald J. Singer; William J. O'Brien

[57] ABSTRACT

A method for preparing unsymmetrical diphosphatetraazacyclooctatetraenes and the novel products produced thereby. The synthesis involves an interaction between an imido-tetraaryl-diphosphinic acid trihalide and a perfluorinated imidoylamidine in the presence of an acid acceptor.

2 Claims, No Drawings

UNSYMMETRICAL DIPHOSPHATETRAAZACYCLOOCTATETRAENES

STATEMENT OF GOVERNMENT INTEREST

The invention described herein may be manufactured and used by or for the Government for governmental purposes without the payment of any royalty thereon.

BACKGROUND OF THE INVENTION

This invention relates to the synthesis of unsymmetrical cyclotetraenes and to novel 8-membered ring heterocyclic compounds produced thereby. More particularly, this invention concerns itself with a novel method for synthesizing 1,3-diphospha-2,4,6,8-tetraazacyclooctatetraens. The resulting compounds find application as antioxidant and anticorrosive additives for perfluorinated-based lubricating fluids and greases as well as other applications requiring the use of antioxidant agents.

The present interest in the utilization of perfluoroalkylether type fluids for high temperature lubicating applications has created a need for effective antioxidant and anticorrosive additives. Although the perfluorinated fluids possess excellent thermal and oxidative characteristics, their potential is somewhat limited due to their tendency to corrode certain metals present in aircraft components. This constitutes a serious drawback in their use as a lubricant since the corroding metal in turn degrades the perfluorinated fluid. This phenomenon tends to occur at temperatures above 550° F. in an oxidative environment.

The need for effective additives to counter the corrosive effect of the perfluorinated fluids on metal parts becomes quite obvious. As a result, a considerable research effort has been undertaken in an attempt to provide new additives which would overcome the corrosion problems encountered when using perfluorinated lubricants in certain high temperature applications within an oxidative environment.

As a result of the concerted research effort referred to above, it has been found that unsymmetrical diphosphatetraazacyclooctatetraenes can be obtained by effecting a reaction between a perfluoroalkylether imidoylamidine and an imido-tetraaryl-diphosphinic acid trichloride. The resulting 8-membered ring compounds are excellent additives for use in perfluorinated lubricants and overcome the corrosion problem associated with the use of these lubricants in high temperature, aerospace applications.

SUMMARY OF THE INVENTION

In accordance with this invention, it has been found that unsymmetrical diphosphatetraazacyclooctatetraenes can be prepared by effecting a reaction between an imido-tetraaryl-diphosphinic acid trihalide and a perfluorinated imidoylamidine in the presence of an acid acceptor. The resulting compounds exhibit properties and provide excellent candidates for high temperature lubricating applications, in addition to providing antioxidant and anticorrosive additives for perfluoroalkylether fluids.

Accordingly, the primary object of this invention is to provide a convenient and efficient method for synthesizing unsymmetrical diphosphatetraazacyclooctatetraenes.

Another object of this invention is to provide a series of novel compounds which can serve as antioxidant and anticorrosive additives for perfluoroalkylether fluids.

Still another object of this invention is to provide a method for synthesizing unsymmetrical diphosphatetraazacyclooctatetraenes through the interreaction of an imido-tetraaryl-diphosphinic acid trihalide and a perfluorinated imidoylamidine.

A further object of this invention is to provide a series of unsymmetrical diphosphatetraazacyclooctatetraenes wherein the two phosphorus atoms are substituted by aromatic groups and the carbon atoms are substituted by either perfluoroalkyl or perfluoroalkylether moieties.

The above and still further objects and advantages of the present invention will become more readily apparent upon consideration of the following detailed disclosure thereof.

DESCRIPTION OF THE PREFERRED EMBODIMENT

The above defined objects of this invention are accomplished by a method of synthesizing unsymmetrical diphosphatetraazacyclooctatetraenes wherein the two phosphorus atoms are substituted by aromatic groups and the carbon atoms are substituted by either perfluoroalkyl or perfluoroalkylether moieties. These materials exhibit a broad range of properties and, depending on substituents, provide candidates for high temperature lubricants and hydraulic fluids, in addition to providing antioxidants and anticorrosion agents for perfluoroalkylether fluids. Other applications will become readily apparent to those skilled in the art.

The general synthesis procedure of this invention can be best represented by the following general equation:

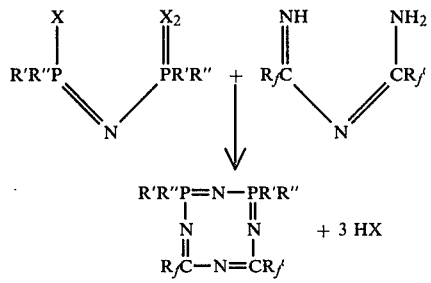

wherein an imido-tetraaryl-diphosphinic acid trihalide is reacted with an equimolar quantity of a perfluorinated imidoylamidine at 30°–100° C. in the presence of an acid acceptor, giving concurrently with hydrogen halide elimination, a diphosphatetraazacyclooctatetraene ring. The substituents $R_f$ and $R'_f$ can be the same or different and can be selected from perfluoroalkyl and perfluoroalkylether groups as represented by the general formulae $C_nF_{2n+1}$, $C_2F_5(OCF_2CF_2)_nOCF_2$, and $C_3F_7[OCF(CF_3)CF_2]_nOCF(CF_3)$. The substituents R' and R'' on the phosphorus can be the same or different aryl groups such as $C_6H_5$, $R-C_6H_4$ (wherein R can be an aryl, alkyl, perfluoroalkyl, or perfluoroalkylether moiety), perfluoroaryl ($C_6F_5$, $R_fC_6F_4$), or any other type of a substituent as should be readily apparent to those skilled in the art. The substituent X on the phosphorus can be either chlorine or bromine while the letter n represents an integer of zero to 20.

The materials used in preparing the unsymmetrical diphosphatetraazacyclooctatetraene products are known compounds that are described in the literature. For example, imido-tetraphenyl-diphosphinic acid trichloride is described by E. Fluck et al in Chem. Ber., 96, 3091 (1963); the perfluoroalkyl and perfluoroalkylether imidoylamidines are disclosed in French Pat. No. 2,166,498 (1973).

The examples presented hereinafter illustrate more specifically the nature of the present invention and provide detailed embodiments of the invention. These embodiments, however, are not to be construed as limiting the invention in any way.

EXAMPLE I

Under nitrogen by-pass, to a solution of imido-tetraphenyl-diphosphinic acid trichloride (1.79 g, 3.65 mmol) in acetonitrile (22 ml) at 50° C. was added a solution of imidoylamidine, $C_3F_7OCF(CF_3)C(=NH)N=C(NH_2)CF(CF_3)-OC_3F_7$, (2.0 g, 3.13 mmol) and triethylamine (1.38 ml, 9.89 mmol) in Freon-113 (7 ml). The mixture was then stirred at 50° C. for 111 hr. Following solvent removal, the Freon-113 soluble 1,3-bis(diphenylphospha)-5,7-bis[CF(CF_3)OCF_3F_7]-2,4,6,8,-tetraazacyclooctatetraene (3.19 g, 80% yield) was crystallized from Freon-113/acetone/pentane; mp 126–126 0.5° C.

Anal. Calcd. for $C_{36}H_{20}F_{22}N_4O_2P_2$: C, 42.37; H, 1.98; F, 40.96; N, 5.49; P, 6.07; O, 3.14; MW, 1020.49.

Found: C, 42.64; H, 2.09; F, 41.33; N, 5.45; P, 6.07; MW, 1050.

The product of Example I is illustrated by the following structural formula

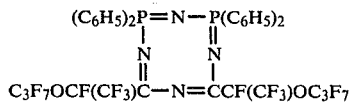

EXAMPLE II

Under nitrogen by-pass, to a solution of the imido-tetraphenyl diphosphinic acid trichloride (1.17 g, 2.38 mmol) in acetonitrile (10 ml) at 50° C. was added dropwise over 1.75 hr a solution of the imidoylamidine, $C_3F_7OCF(CF_3)-CF_2OCF(CF_3)C(=NH)-N=C(NH_2)CF(CF_3)OCF_2CF(CF_3)OC_3F_7$, (2.05 g, 2.11 mmol) and triethylamine (0.98 ml, 7.03 mmol) in Freon-113 (18 ml) The resulting mixture was heated at ~50° C. for 142 hr. After solvent removal the residue was tritiated with Freon-113 (4×10 ml) and then filtered through a 1.5×5 cm column of Woelm neutral alumina. 1,3-Bis(diphenylphospha)-5,7-bis[CF(CF_3)OCF_2CF(CF_3)OC_3F_7]-2,4,6,8-tetraazacyclooctatetraene thus obtained (2.80 g, 98% yield) was distilled in vacuo, bp 146°–148° C./0.001 mm Hg.

Anal. Calcd. for $C_{42}H_{20}F_{34}N_4N_4P_2$: C, 37.30; H, 1.49; F, 47.76; N, 4.14; P, 4.58; O, 4.73; MW, 1352.55.

Found: C, 38.29; H, 1.55; F, 48.82; N, 4.23; P, 3.94; MW, 1400.

The above cyclooctatetraene exhibited good thermal oxidative stability as shown by 1% and 4% volatilization after 24 hour heat treatment in air at 235° and 316° C., respectively.

The product of Example II is illustrated by the following structural formula:

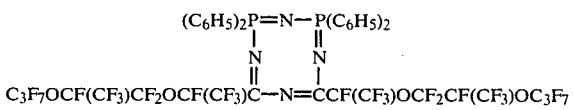

The 1,3-bis(diphenylphospha)-5,7-bis[CF(CF_3)OCF_2CF (CF_3)OC_3F_7]-2,4,6,8-tetraazacyclooctatetraene was found to effectively inhibit oxidation of perfluoroalkylether fluids of the type disclosed in U.S. Pat. No. 3,393,151 and to prevent corrosion of various metals by these fluids. For example, a 1% by weight solution of this cyclooctatetraene in such a fluid decreased oxygen consumption to zero and volatile products formation by a factor of 330 during a 24 hour exposure to oxygen at 600° F. as compared to an identical treatment of the fluid in the absence of the additive. In addition, an M-50 coupon surface in the presence of the additive appeared unchanged, whereas in the absence of any additive, under otherwise identical conditions, the surface becomes covered with deeply colored irregular deposits. These data are summarized below in Table I.

TABLE I

Degradation of Krytox 143 AC Fluid (a product of E. I. du Pont de Nemours and Co.) in the Presence of M-50 Alloy Coupon at 600° F. in Oxygen for 24 hr[a]

| Fluid Used g | Additive | Oxygen Consumed Total | | | Total Products Formed | |
|---|---|---|---|---|---|---|
| | | mg | %[b] | mg/g[c] | mg | mg/g[d] |
| 12.13 | none | 70.8 | 24.6 | 5.84 | 576.7 | 47.54 |
| 13.33 | 1%[e] $C_{42}H_{20}F_{34}N_4O_4P_2$ | 0.0 | 0.0 | 0.0 | 1.8 | 0.14 |

[a] the apparatus consisted of a sealed glass tube wherein the metal coupon was suspended in the fluid; the test was conducted in pure oxygen; at the conclusion of the test, the oxygen was measured and the products were collected and measured.
[b] Percent of oxygen available.
[c] Oxygen consumed in mg/g Krytox employed.
[d] Products formed in mg/g Krytox employed.
[e] The percent is weight percent of additive per weight of Krytox fluid.

While the invention has been described with particularity in reference to specific embodiments thereof, it is to be understood that the disclosure is for the purpose of illustration only and that various modifications and alterations may be made without departing from the spirit of the invention, the scope of which is defined by the appended claims.

What is claimed is:

1. The compound 1,3-bis(diphenylphospha)-5,7-bis[CF(CF_3)OC_3F_7]-2,4,6,8-tetraazacyclooctatetraene.

2. The compound 1,3-bis(diphenylphospha)-5,7-bis [CF(CF_3)OCF_2CF(CF_3)OC_3F_7]-2,4,6,8-tetraazacyclooctatetraene.

* * * * *